United States Patent [19]
Roessler et al.

[11] Patent Number: 5,516,567
[45] Date of Patent: May 14, 1996

[54] ATTACHMENT TAPE FINGER TAB

[75] Inventors: Thomas H. Roessler, Menasha; Mary P. Jordan; Carmen C. Donovan, both of Neenah, all of Wis.

[73] Assignee: Kimberly-Clark Corporation, Neenan, Wis.

[21] Appl. No.: 154,885

[22] Filed: Nov. 18, 1993

Related U.S. Application Data

[62] Division of Ser. No. 923,066, Jul. 31, 1992, Pat. No. 5,288,546.

[51] Int. Cl.$^6$ .............................. A41B 13/00; B32B 3/06
[52] U.S. Cl. .................... 428/40.1; 428/42.2; 428/42.3; 428/192; 428/194; 428/220; 428/354; 428/913; 604/389; 604/390
[58] Field of Search ............................ 428/40, 41, 42, 428/194, 192, 220, 354, 913; 604/389, 390

[56] References Cited

U.S. PATENT DOCUMENTS

| | | | |
|---|---|---|---|
| 2,714,889 | 8/1955 | Chambers | 128/287 |
| 3,616,114 | 10/1971 | Hamaguchi et al. | 161/39 |
| 3,776,234 | 12/1973 | Hoey | 128/287 |
| 3,848,594 | 11/1974 | Buell | 128/284 |
| 3,862,634 | 1/1975 | Small | 128/284 |
| 3,893,460 | 7/1975 | Karami | 128/287 |
| 3,901,236 | 8/1975 | Assarsson et al. | 128/284 |
| 3,931,666 | 1/1976 | Karami | 24/73 VA |
| 3,937,221 | 2/1976 | Tritsch | 128/287 |
| 3,948,258 | 4/1976 | Karami | 128/287 |
| 3,948,267 | 4/1976 | Karami | 128/287 |
| 3,948,268 | 4/1976 | Karami | 128/287 |
| 3,978,860 | 9/1976 | Stima | 128/284 |
| 3,999,545 | 12/1976 | Milnamow | 128/284 |
| 4,005,712 | 2/1977 | Karami | 128/287 |
| 4,005,713 | 2/1977 | Mesek | 128/287 |
| 4,010,753 | 3/1977 | Tritsch | 128/284 |
| 4,047,530 | 9/1977 | Karami | 128/287 |
| 4,049,001 | 9/1977 | Tritsch | 604/390 |
| 4,050,462 | 9/1977 | Woon et al. | 128/287 |
| 4,051,853 | 10/1977 | Egan, Jr. | 128/287 |
| 4,055,182 | 10/1977 | Mack | 128/287 |
| 4,058,125 | 11/1977 | Ness | 128/287 |
| 4,067,337 | 1/1978 | Ness | 128/287 |
| 4,074,716 | 2/1978 | Schaar | 128/287 |
| 4,076,663 | 2/1978 | Masuda et al. | 260/17.4 |
| 4,136,698 | 1/1979 | Mesek | 128/287 |
| 4,144,887 | 3/1979 | Milnamow | 128/287 |
| 4,186,744 | 2/1980 | Ness | 128/287 |
| 4,210,144 | 7/1980 | Sarge, III et al. | 128/287 |
| 4,227,530 | 10/1980 | Schatz | 128/287 |
| 4,286,082 | 8/1981 | Tsubakimoto et al. | 526/240 |
| 4,299,223 | 11/1981 | Cronkrite | 128/287 |

(List continued on next page.)

FOREIGN PATENT DOCUMENTS

| | | |
|---|---|---|
| 80713/82 | 2/1982 | Australia. |
| 0148587 | 7/1985 | European Pat. Off.. |
| 0247855 | 12/1987 | European Pat. Off.. |
| 0396050 | 11/1990 | European Pat. Off.. |
| 2557778 | 7/1985 | France. |
| 9112007 | 6/1984 | Japan ................. 604/389 |
| 2114449 | 8/1983 | United Kingdom. |
| 2206506 | 1/1989 | United Kingdom. |
| 90/07426 | 7/1990 | WIPO. |

Primary Examiner—Nasser Ahmad
Attorney, Agent, or Firm—Paul Yee

[57] ABSTRACT

A distinctive article has first and second waistband sections, and an intermediate section which interconnects the waistband sections. The article comprises a backsheet layer, a liquid permeable topsheet layer superposed in facing relation with the backsheet layer, and an absorbent body interposed between the backsheet and topsheet layers. At least one adhesive tape member connects to the first waistband section. The tape member has a factory-bond section for connecting the tape member to the first waistband section, and a user-bond section for securing the article on a wearer. The user-bond section connects to a finger tab which includes a non-securing grasping section thereof. In particular embodiments, the grasping section can comprise a layer of absorbent material.

16 Claims, 10 Drawing Sheets

U.S. PATENT DOCUMENTS

| | | | |
|---|---|---|---|
| 4,522,853 | 6/1985 | Szonn et al. | 428/40 |
| 4,540,415 | 9/1985 | Korpman | 604/390 |
| 4,552,560 | 11/1985 | Tritsch | 604/390 |
| 4,568,344 | 2/1986 | Suzuki et al. | 604/389 |
| 4,699,823 | 10/1987 | Kellenberger et al. | 428/219 |
| 4,704,116 | 11/1987 | Enloe | 604/385 A |
| 4,726,971 | 2/1988 | Pape et al. | 428/40 |
| 4,753,646 | 6/1988 | Enloe | 604/385 R |
| 4,753,649 | 6/1988 | Pazdernik | 604/389 |
| 4,778,701 | 10/1988 | Pape | 428/41 |
| 4,801,480 | 1/1989 | Panza et al. | 428/40 |
| 4,883,480 | 11/1989 | Huffman | 604/378 |
| 4,916,005 | 4/1990 | Lippert et al. | 428/192 |
| 5,024,672 | 6/1991 | Widlund | 604/390 |
| 5,034,007 | 7/1991 | Igaue et al. | 604/365 |

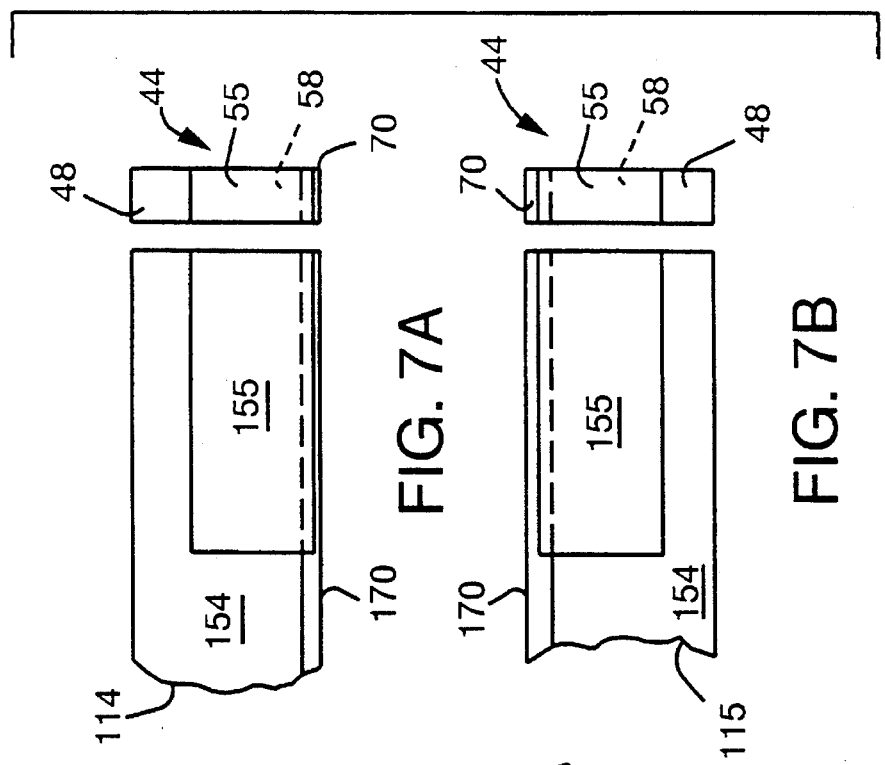
FIG. 7A
FIG. 7B
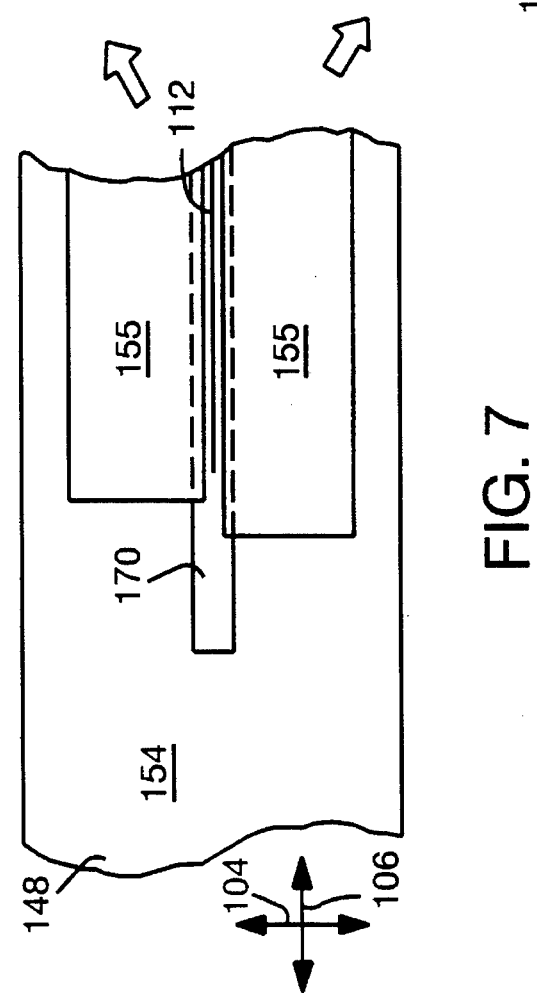
FIG. 7

5,516,567

ATTACHMENT TAPE FINGER TAB

This is a divisional application of application Ser. No. 07/923,066, filed on Jul. 31, 1992, now U.S. Pat. No. 5,288,546.

FIELD OF THE INVENTION

The present invention relates to fastening systems for disposable garments, such as caps, gowns, diapers, shoe covers, incontinence garments and the like. More particularly, the present invention relates to an adhesive tape fastener for disposable absorbent articles, such as diapers and incontinence garments.

BACKGROUND OF THE INVENTION

Conventional disposable absorbent articles have typically employed adhesive fastening tapes for securing the article on a wearer. For example, see U.S. Pat. No. 2,714,889 issued Aug. 9, 1955, to U. Chambers and U.S. Pat. No. 4,050,462 issued Sep. 27, 1977, to L. Woon et el. Conventional adhesive tape fastening systems have employed adhesive tape tabs which include a non-adhesive section located at the distal free end of the tape tab. This adhesive-free region has typically referred to as a finger tab for facilitating the grasping of the end of the adhesive tape. For example, U.S. Pat. No. 4,055,187 issued Oct. 25, 1977, to R. Mack describes an end tab formed by folding the end region of the tab back onto itself. Other adhesive tape structures have included a finger tab formed by placing a separate piece of material at the terminal free end of the tape member. For example, see U.S. Pat. No. 4,726,971 issued Feb. 23, 1988, to P. Pape et el.; U.S. Pat. No. 3,616,114 issued Oct. 26, 1971, to T. Hamaguchi et al.; U.S. Pat. No. 4,801,480 issued Jan. 31, 1989, to V. Panza et al.

The finger tabs on conventional adhesive fastening tapes, such as those described above, have had relatively small or relatively narrow grasping areas. As a result, the finger tabs can be hard to locate and the adhesive bearing, securing sections of the tape have been susceptible to undesired contamination from oils or powders carried on the fingers of the user.

BRIEF DESCRIPTION OF THE INVENTION

Generally stated, the present invention provides a distinctive adhesive tape which includes a tape member having a factory-bond section for connecting the tape member to an article, and a user-bond section for adhesively securing the article on a wearer. The user-bond section is connected to a finger tab which provides a non-securing grasping section. In particular aspects of the invention, the grasping section comprises a distinctively configured exposed layer of absorbent material.

One aspect of the invention comprises an article having first and second waistband sections, and an intermediate section which interconnects the waistband sections. The article includes a backsheet layer, a liquid permeable topsheet layer superposed in facing relation with the backsheet layer, and an absorbent body interposed between the backsheet and topsheet layers. At least one adhesive tape member is connected to the first waistband section. The tape member has a factory-bond section for connecting the tape member to the first waistband section and a user-bond section for selectively connecting the tape to a complementary region of the second waistband section to secure the article on a wearer. The user-bond section of the tape connects to a finger tab which includes a non-securing grasping section thereof. The grasping section can comprise a layer of absorbent material or a layer having a relatively higher level of grippability, or both.

In a method aspect of the invention, a process for forming a tape fastener, includes the steps of providing a web of substrate material having a layer of adhesive thereon, and assembling a web of finger tab material in an overlapping relation with a selected side edge of said substrate material to form a composite web. The composite web can then be separated along a cross-dimension thereof to form a plurality of individual tape fasteners.

In another method aspect of the invention, a process for forming a tape fastener includes the steps of providing a web of substrate material having a layer of adhesive thereon, and assembling a web of finger tab material in an overlapping relation with a selected medial portion of said substrate material to form a composite web. The composite web is separated along a separation line which extends generally along a length dimension of said composite, and the composite web is separated along a cross-dimension thereof to form a plurality of tape fasteners.

The distinctive adhesive tape fastening system of the present invention can advantageously provide an improved adhesive tape fastening system wherein the individual adhesive tapes are easier to locate and grasp, and are less susceptible to contamination by oils, powders, debris or other undesired contaminants which might interfere with the adhesion of the adhesive tapes onto the fastening zone of the article.

The method of the invention can provide an efficient technique for rapidly producing the taping system of the invention. In particular configurations, the method can be carried out in-line with the process for manufacturing the associated article that employs the tape fastening system, thereby helping to reduce costs.

BRIEF DESCRIPTION OF THE DRAWINGS

The present invention will be more fully understood and further advantages will become apparent when reference is made to the following detailed description of the invention and the drawings, in which:

FIGS. 7–7B representatively show another method of producing an interconnected plurality of adhesive tapes constructed in accordance with the invention;

DETAILED DESCRIPTION OF THE INVENTION

The various embodiments of the invention will be described in the context of a disposable absorbent article, such as a disposable diaper. It is, however, readily apparent that the present invention could also be employed with other articles, such as caps, gowns, shoe covers, incontinence garments and the like.

Typically, disposable articles are intended for limited use and are not intended to be laundered or otherwise cleaned for reuse. For example, a disposable diaper is discarded after it has become soiled by the wearer.

Figure 1:
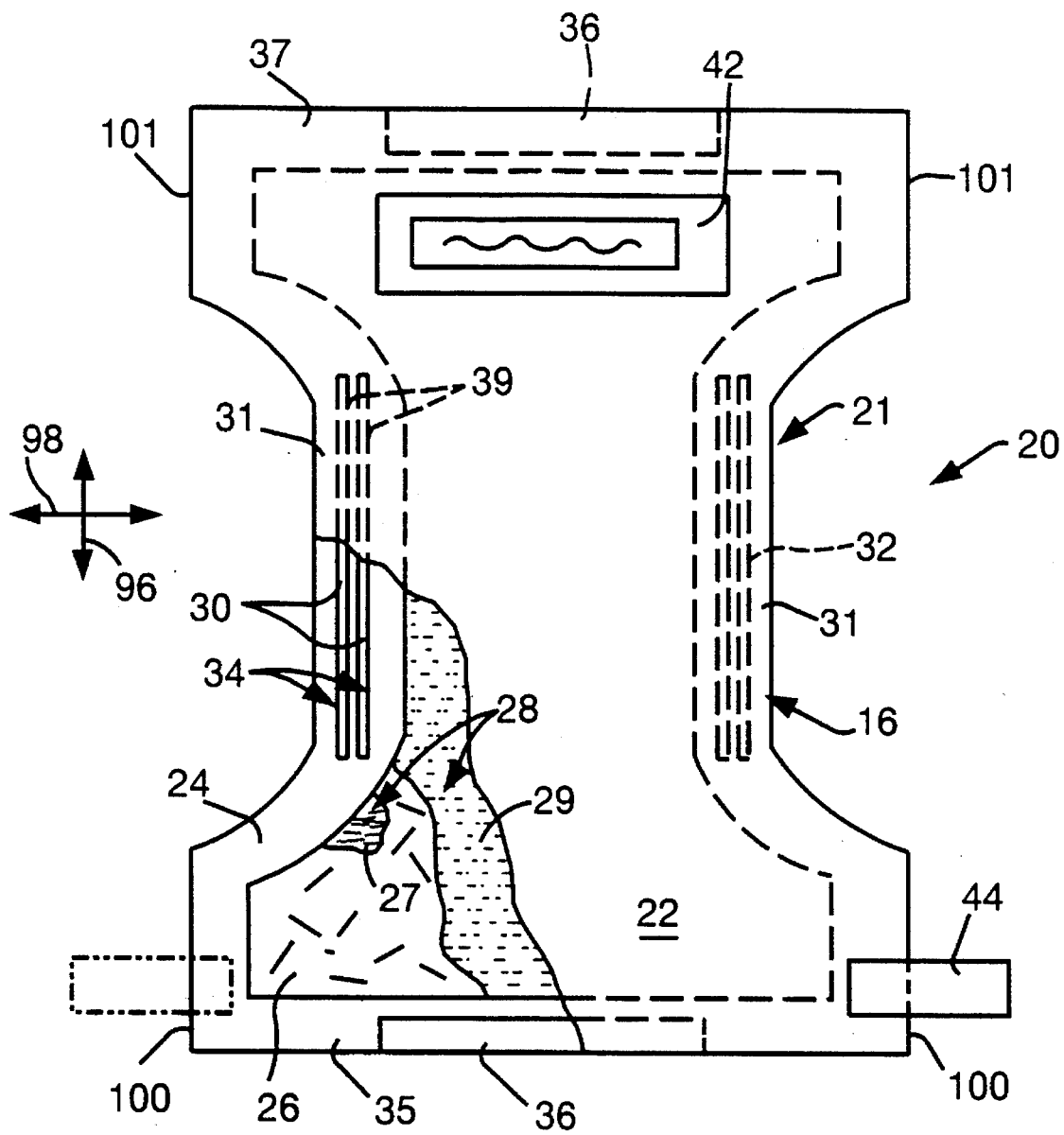
FIG. 1 representatively shows a partially cut-away, plan view of a diaper article which incorporates the adhesive tapes of the present invention.

With reference to FIG. 1, a representative disposable diaper article is shown in its fully extended condition with all of the elasticized gathers stretched out and removed. An article, such as disposable diaper 20, has a first waistband section 35, a second waistband section 37, and an intermediate section 21 which interconnects the waistband sections. The article comprises a backsheet layer 22, a liquid permeable topsheet layer 24 superposed in facing relation with the backsheet layer, and an absorbent body 26 interposed between the backsheet and topsheet layers. At least one adhesive tape fastener 44, and preferably a complementary, opposing pair thereof, are connected to first waistband section 35 of diaper 20.

Figure 2:
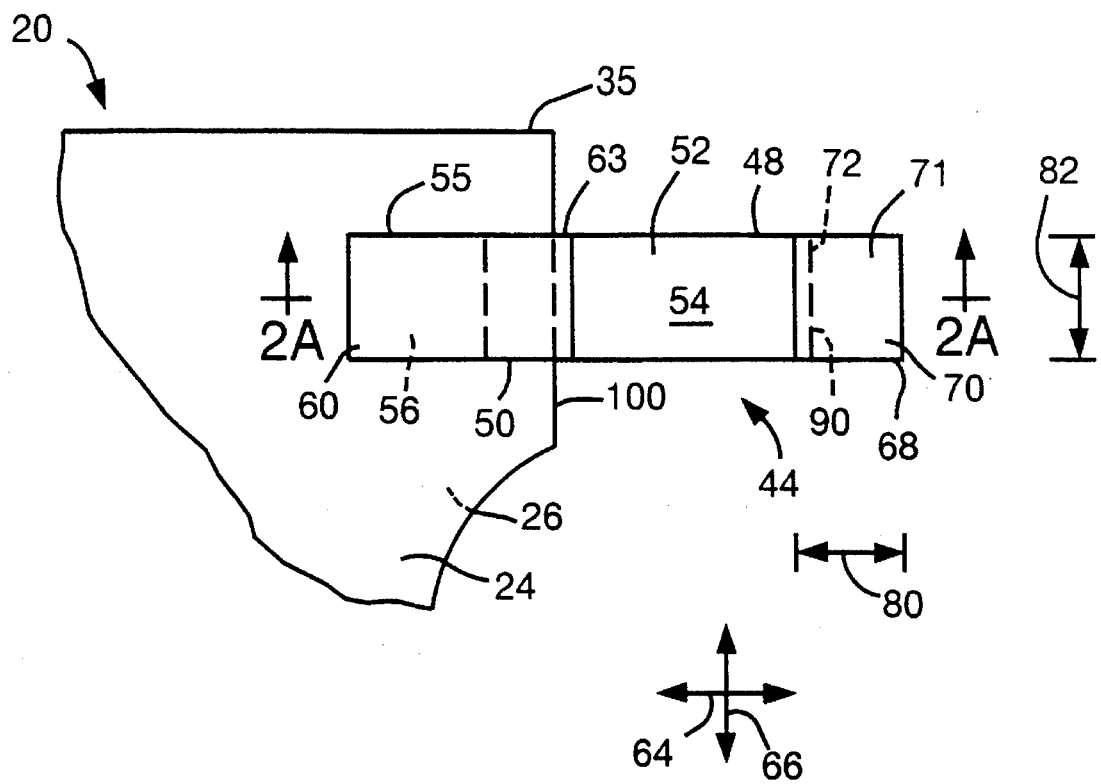
FIGS. 2–2A representatively show an adhesive tape of the invention.
Figure 2A:
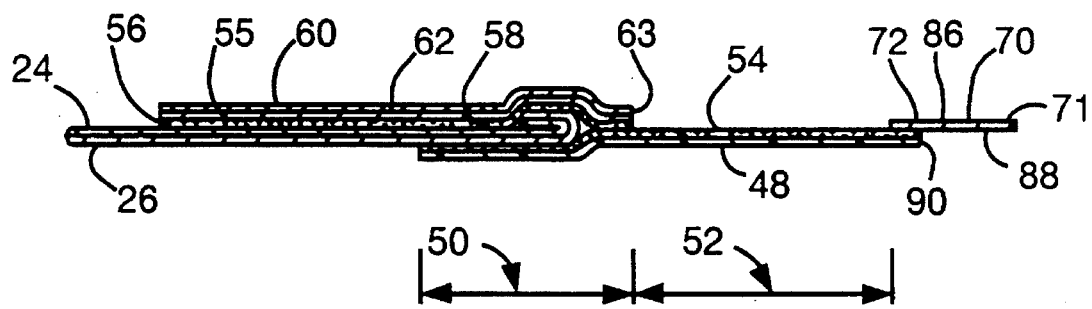

With reference to FIGS. 2–2A, a tape fastener 44 can comprise a tape substrate member 48 which includes a factory-bond section 50 for connecting the tape substrate member to a selected portion of diaper 20, and a user-bond section 52 for connecting and securing the waistband sections of the diaper about the body of a wearer. User-bond section 52 is operably connected to a finger tab 70 which includes a substantially non-securing grasping section 71 thereof. The grasping section, in a particular aspect of the invention, comprises a layer of absorbent material, such as a nonwoven fabric.

Figure 3:
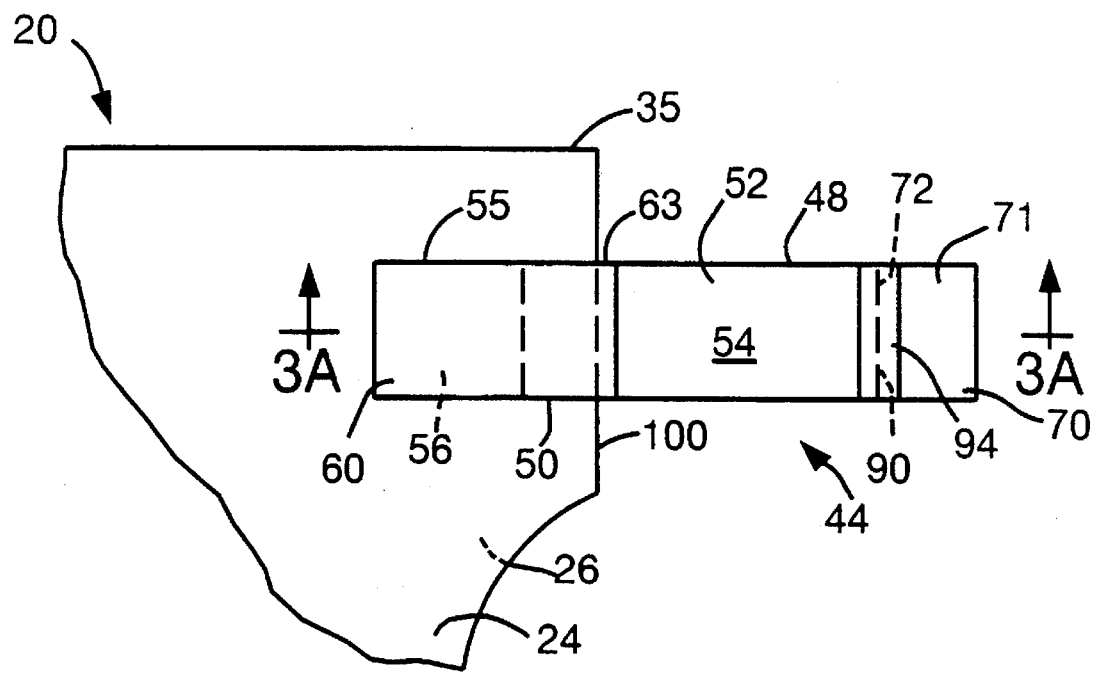
FIGS. 3–3A representatively show an adhesive tape of the present invention which includes a Supplemental adhesive region.
Figure 3A:
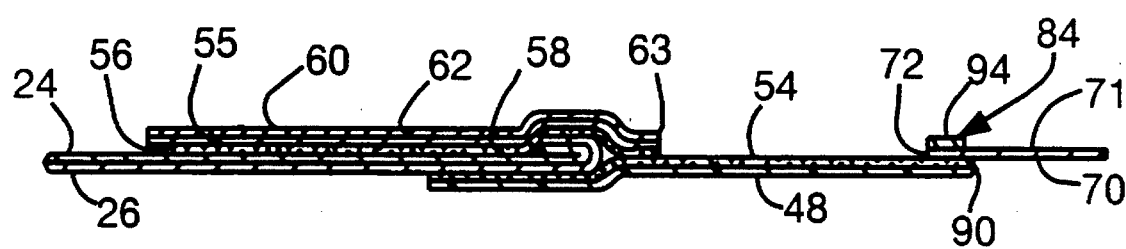

As representatively shown in FIGS. 3–3A, the user-bond section of a tape fastener 44 can include a primary layer of adhesive 54, and can be connected to a finger tab 70 which has a substantially non-securing, grasping section 71 thereof. The finger tab connects to substrate member 48 along a fixedly attached end region 72 of the finger tab. Fixed end region 72, which extends along the width dimension and preferably extends along the entire width of tape substrate 48, includes a supplemental adhesive layer 94 thereon. The supplemental adhesive has a relatively higher peel strength value than primary adhesive 54, as determined with respect to adhesion to an appointed tape securement zone of the article, such as landing zone patch 42.

Figure 4:
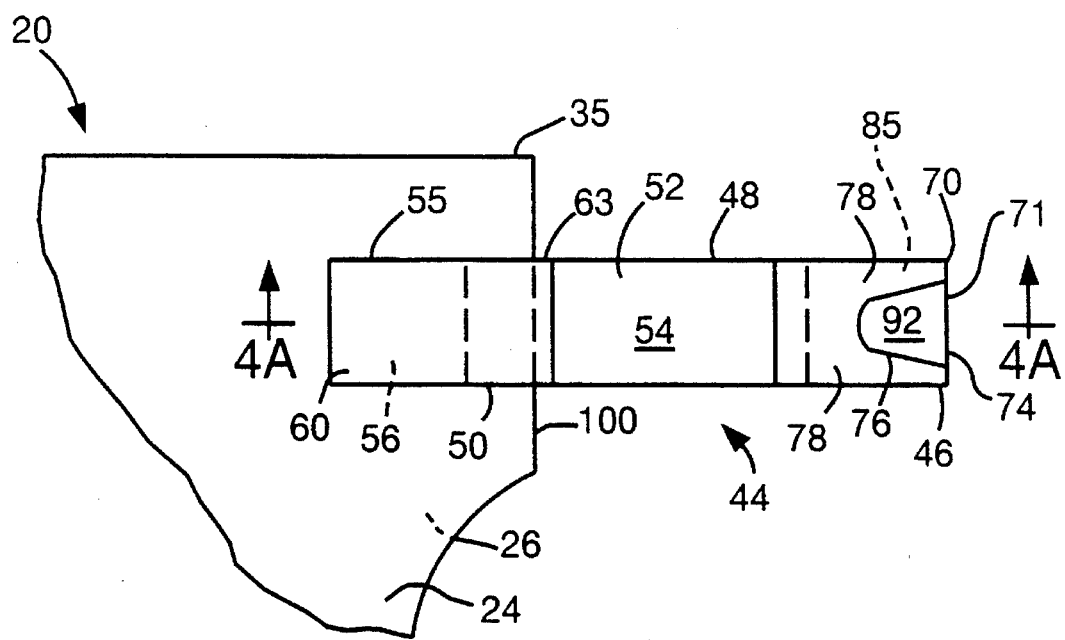
FIGS. 4–4A representatively show an adhesive tape of the invention which includes an indented region at a terminal, free end thereof.
Figure 4A:
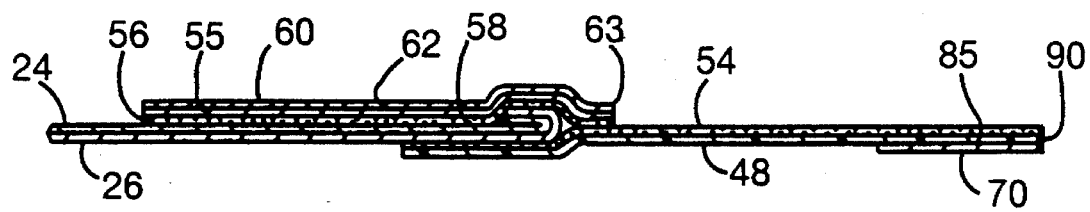

With reference to FIGS. 4–4A, another aspect of the invention can incorporate an adhesive tape 44 wherein user-bond section 52 of tape substrate member 48 includes a terminal end region 90 which has a generally concave peripheral outline 76. The concave outline defines an indented area 92 which is substantially free of exposed adhesive and extends inwardly from a longitudinally terminal edge 74 of tape substrate member 48.

Figure 5:
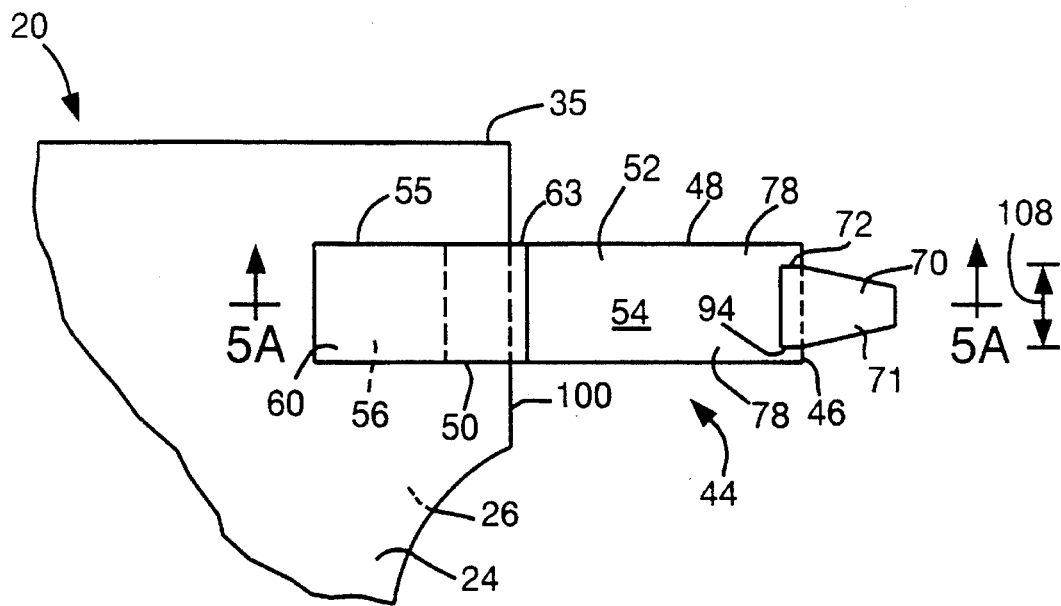
FIGS. 5–5B representatively show an embodiment of the invention having a finger tab with a curvilinear peripheral edge contour and a relatively smaller, reduced width which can be deployed in alternative modes.
Figure 5A:
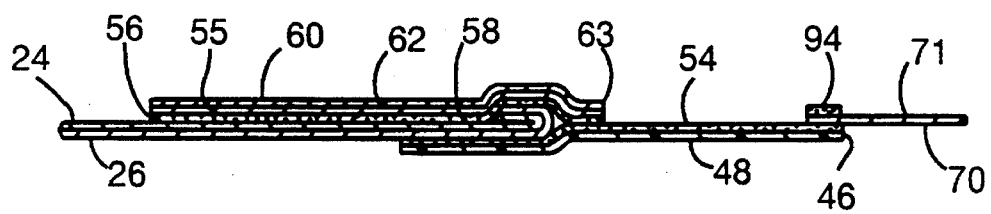
Figure 5B:
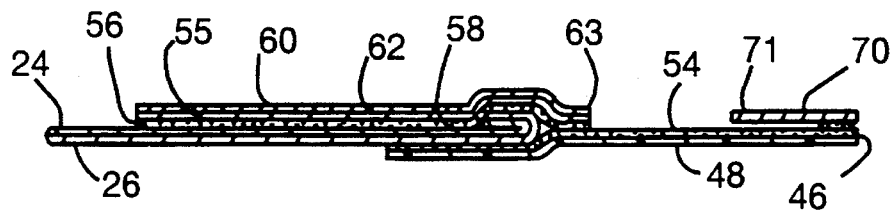

With reference to FIGS. 5–5B, yet another aspect of the invention incorporates a tape fastener 44 which comprises a tape substrate member 48 with a user-bond section 52 including a primary layer 54 of adhesive thereon. The user-bond section connects to a finger tab 70 which has a substantially non-securing grasping section 71 thereof. The finger tab connects to tape substrate member 48 along a fixed end region 72 of the finger tab. At least a portion of fixed end region 72 includes a supplemental layer 94 of adhesive thereon. Supplemental adhesive 94 has a relatively higher peel strength value than primary adhesive 54, as determined with respect to adhesion onto an appointed tape securement zone, such as landing zone patch 42, of diaper 20. Grasping section 71 can be selectively configured in an extended position which reaches out past the terminal edge 46 of substrate 48 (FIG. 5A), or in a retracted position which is folded over against the adhesive-bearing side of the substrate (FIG. 5B).

Diaper 20 may have any desired shape, such as rectangular, I-shaped, a generally hourglass shape, or a T-shape. With the T-shape, the crossbar of the "T" may comprise the front waistband portion of the diaper or may comprise the rear waistband portion of the diaper. The diaper has a length dimension 96 and a width dimension 98, as representatively shown in FIG. 1.

Backsheet 22 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 22 prevents the exudates contained in absorbent body 26 from wetting articles, such as bedsheets and overgarments, which contact diaper 20. In particular embodiments of the invention, backsheet 22 is a polyethylene film having a thickness of from about 0.012 millimeters (0.5 mil) to about 0.051 millimeters (2.0 mils). In the shown embodiment, the backsheet is a film having a thickness of about 1–1.5 mil. For example, the backsheet film can have a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. Backsheet 22 typically provides the outer cover of the article. Optionally, however, the article may comprise a separate outer cover member which is in addition to the backsheet.

Backsheet 22 may alternatively be composed of a microporous, "breathable" material which permits gasses, such as water vapor, to escape from absorbent body 26 while substantially preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise be provided with a matte finish to exhibit a more aesthetically pleasing appearance.

The size of backsheet 22 is typically determined by the size of absorbent body 26 and the particular diaper design selected. Backsheet 22, for example, may have a generally T-shape, a generally I-shape or a modified hourglass shape, and may extend beyond the terminal edges of absorbent body 26 by a selected distance, such as a distance of at least about 1.27 cm (about 0.5 in). In particular embodiments of the invention, backsheet can extend beyond the edges of absorbent body 26 by a distance within the range of about 1.3 centimeters to 2.5 centimeters (about 0.5 to 1.0 inch).

Topsheet 24 presents a body-facing surface which is compliant, soft-feeling, and non-irritating to the wearer's skin. Further, topsheet 24 can be less hydrophilic than absorbent body 26, and is sufficiently porous to be liquid permeable, permitting liquid to readily penetrate through its thickness to reach the absorbent body. A suitable topsheet 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 24 is typically employed to help isolate the wearer's skin from liquids held in absorbent body 26.

Various woven and nonwoven fabrics can be used for topsheet 24. For example, the topsheet may be composed of a meltblown or spunbonded web of polyolefin fibers. The topsheet may also be a bonded-carded-web composed of natural fibers, synthetic fibers or combinations thereof.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 24 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant.

In the shown embodiment of diaper 20, topsheet 24 and backsheet 22 are generally coextensive and have length and width dimensions which are generally larger than the corresponding dimensions of absorbent body 26. Topsheet 24 is associated with and superimposed on backsheet 22, thereby defining the periphery of diaper 20.

Topsheet 24 and backsheet 22 are connected or otherwise associated together in an operable manner. As used herein, the term "associated" encompasses configurations in which topsheet 24 is directly joined to backsheet 22 by affixing topsheet 24 directly to backsheet 22, and configurations wherein topsheet 24 is joined to backsheet 22 by affixing topsheet 24 to intermediate members which in turn are affixed to backsheet 22. Topsheet 24 and backsheet 22 can be affixed directly to each other in the diaper periphery by attachment means (not shown) such as an adhesive bonds, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 24 to backsheet 22. It should be readily appreciated that the above-described attachment means may also be employed to interconnect and assemble together the other component parts of the article.

Absorbent body 26 can comprise an absorbent pad composed of selected hydrophilic fibers and high-absorbency particles. The absorbent body is positioned between topsheet 28 and backsheet 22 to form diaper 20. The absorbent body has a construction which is generally compressible, conformable, non-irritating to the wearer's skin, and capable of absorbing and retaining liquid body exudates. It should be understood that, for purposes of this invention, the absorbent body may comprise a single, integral piece of material, or alternatively, may comprise a plurality of individual separate pieces of material which are operably assembled together.

Various types of wettable, hydrophilic fibrous material can be used to form the component parts of absorbent body 26. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System. When measured with this system in accordance with the procedure described in detail herein below, fibers having contact angles less than 90° are designated "wettable", while fibers having contact angles greater than 90° are designated "nonwettable".

Absorbent body 26 can comprise a matrix of hydrophilic fibers, such as a web of cellulosic fluff, mixed with particles of high-absorbency material. In particular arrangements, absorbent body 26 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference to the extent that it is consistent with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly-(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et el. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent body 26 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 26.

Preferred for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and preferably is within the range of about 550–750 gsm to provide desired performance.

To improve the containment of the high-absorbency material, absorbent body 26 can include an improved overwrap, such as wrap sheet 28, placed immediately adjacent and around absorbent body 26. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrap which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 28, or at least the bodyside layer of the wrap sheet, may comprise a meltblown web composed of meltblown polypropylene fibers having a fiber size of about 5 micrometers and arranged to form a basis weight within the range of about 8–20 gsm.

Another example of absorbent wrap 28 may comprise a low porosity cellulosic tissue web composed of an approximately 50/50 blend of hardwood/softwood fibers. The tissue has a 13 lb basis weight at the reel and a porosity of about 90 cfs/sq. ft.

Absorbent wrap 28 may comprise a multi-element wrap-sheet which includes a separate bodyside wrap layer 27 and a separate outerside wrap layer 29, each of which extends past all or some of the peripheral edges of absorbent body 26. Such a configuration of the wrap sheet can, for example, facilitate the formation of a substantially complete sealing and closure around the peripheral edges of absorbent body 26. In the back waistband portion of the illustrated diaper, the absorbent wrap may also be configured to extend an increased distance away from the periphery of the absorbent body to add opacity and strength to the back ear sections of the diaper. In the illustrated embodiment, the bodyside and outerside layers of absorbent wrap 28 extend at least about ½" inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 28 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Leg elastic members 30 and 32 are located in the lateral side margins 31 of diaper 20 and are arranged to draw and hold diaper 20 against the legs of the wearer. The elastic members are secured to diaper 20 in an elastically contractible condition so that in a normal under strain configuration, the elastic members effectively contract against diaper 20. The elastic members can be secured in an elastically contractible condition in at least two ways, for example, the elastic members may be stretched and secured while diaper 20 is in an uncontracted condition. Alternatively, diaper 20 may be contracted, for example, by pleating, and the elastic members secured and connected to diaper 20 while the elastic members are in their unrelaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 20. Alternatively, elastic members 34 may extend the entire length of diaper 20, or any other length suitable providing the arrangement of elastically contractible lines desired for the particular diaper design.

Elastic members 30 and 32 may have any of a multitude of configurations. For example, the width of the individual elastic members 30 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 20 with sprayed or swirled patterns of hotmelt adhesive.

In the illustrated embodiments of the invention, leg elastic members 30 and 32 may comprise a carrier sheet (not shown) to which are attached a grouped set of elastics composed of a plurality of individual elastic strands 39. The elastic strands may intersect or be interconnected, or be entirely separated from each other. The shown carrier sheet may, for example, comprise a 0.002 cm thick film of unembossed polypropylene material. The shown elastic strands can, for example, be composed of Lycra elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, leg elastics 30 and 32 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance within the range of about 0–8 cm toward either the front or rear waistband of the diaper to provide desired fit and appearance. In particular embodiments of the invention, the innermost point (apex) of the set of curved elastics can be offset about 0–12 cm towards the front or rear waistband of the diaper, and the outwardly bowed reflexed-portion can be positioned toward the diaper front waistband.

In the shown embodiment, diaper 20 includes a waist elastic 36 positioned in the longitudinal margins of either or both of front waistband 37 and rear waistband 35. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the disclosure of which is hereby incorporated by reference to the extent that it is consistent herewith.

Diaper 20 can also include a pair of elasticized containment flaps which extend longitudinally along the length dimension 96 of the diaper. The containment flaps are typically positioned laterally inboard from leg elastics 30 and 32, and substantially symmetrically placed on each side of the lengthwise, longitudinal centerline of the diaper. Examples of suitable containment flap constructions are described in U.S. Pat. No. 4,704,116 issued Nov. 3, 1987, to K. Enloe, the disclosure of which is hereby incorporated by reference to the extent that it is consistent herewith. The containment flaps may be composed of a wettable or a non-wettable material, as desired. In addition, the containment flap material may be permeable to vapor or permeable to both vapor and a liquid.

In an optional, alternative embodiment of the invention, diaper 20 may include elasticized waist flaps, such as those described in U.S. Pat. No. 4,753,646 issued Jun. 28, 1988, to K. Enloe, the disclosure of which is hereby incorporated by reference to the extent that it is consistent herewith. Similar to the construction of the containment flaps, the waist flaps may be composed of a wettable or non-wettable material, as desired. The waist flap material may be permeable to vapor, or permeable to both vapor and liquid.

To provide a refastenable adhesive taping system, diaper 20 can include a supplemental landing zone patch 42, which provides a target zone for receiving an adhesive attachment of tape fasteners 44 thereon. In the illustrated embodiment of the invention, landing zone patch 42 is positioned on the outward surface of backsheet 22 and is located on the second, front waistband portion 37 of the diaper. Landing zone patch 42 is constructed of a suitable material, such as polypropylene, polyester, or the like, and is configured and arranged to accept a secure adhesion of tape fasteners 44. In addition, the landing zone patch and the tape fasteners are cooperatively constructed and arranged to provide a releasable adhesion which allows the tape fastener to be removed from the landing zone patch for repositioning and re-adhesion without tearing or excessively deforming the material of backsheet 22. For example, a suitable tape landing zone construction is described in U.S. Pat. No. 5,024,672 issued Jun. 18, 1991, to L. Widlund. A further construction of a tape landing zone patch is described in U.S. Pat. No. 4,753,649 issued to Pazdernik, the disclosure of which is hereby incorporated by reference to the extent that it is consistent herewith.

In various embodiments of the invention, a tape fastener 44 can be located at either or both of lateral ends 100 and 101 of either or both of waistbands 35 and 37, respectively. The representatively shown embodiment has the tape fasteners located at the terminal side edges of rear waistband 35.

With reference to FIGS. 2–2A, Tape fastener 44 includes a substrate member 48 and a primary adhesive layer 54. Substrate member 48 can be composed of a suitable polymer film material, such as polypropylene. The material comprising substrate member 48 may be opaque, translucent or transparent, as desired, and may include graphics thereon. Optionally, the material may be tinted and/or textured. The material may also be selectively embossed.

Tape fastener 44 has a factory-bond region 50 which is appointed for securement onto the desired section of its associated article during the manufacture of the article. Tape fastener 44 also includes a user-bond region 52 which is appointed for adhesively securing the article on a wearer during use. In the illustrated embodiment of diaper 20, the factory-bond region 50 of tape fastener 44 is attached to the lateral ends of rear waistband 35, and the user-bond region 52 of the tape fastener is employed to attach the lateral ends of rear waistband 35 to the corresponding lateral ends of front waistband 37 to secure the diaper about the waist of a child. User-bond section 52 connects to a finger tab 70 which includes a substantially non-attaching grasping section 71 thereof. The grasping section comprises a layer of exposed absorbent material. Tape fastener 44 is configured with at least a portion of the exposed absorbent material operably positioned and arranged to face in the same direction as an inward face of the tape fastener. Typically, the inward face of the tape fastener has primary adhesive layer 54 applied thereon.

In a particular aspect of the invention, the grasping section 71 of finger tab region 70 is constructed from a material having a Gurley stiffness value of not more than about 700 milligrams (mg). The grasping section preferably is constructed with a Gurley stiffness value of not more than about 500 mg, and more preferably, is constructed with a Gurley stiffness value of not more than about 400 mg. For example, in particular embodiments where the grasping section 71 of the finger tab is laminated or otherwise assembled to other components, such as substrate 48, to provide a composite grasping section (e.g. FIG. 8B), the resultant grasping section can be composed of a composite material having a Gurley stiffness value of not more than about 700 mg. Preferably the composite stiffness value is not more than about 500 mg, and more preferably is not more than about 400 mg.

A suitable technique for determining Gurley stiffness is set forth in TAPPI T543 PM-84. For the purposes of the present invention, the dimensions of the sample employed for determining Gurley stiffness measured 1.5 inch in length and 1.0 inch in width.

A primary adhesive layer 54 is disposed upon a selected facing surface of substrate member 48. The portion of adhesive positioned on factory-bond 50 can be employed to assemble tape fastener 44 onto diaper 20 during the manufacture of the diaper. The portion of adhesive layer 54 located on user-bond region 52 can be employed to secure the diaper onto an infant. The particular adhesive parameters of adhesive layer 54 can be selected and tailored to meet desired adhesive properties, such as adhesive shear strength and adhesive peel strength.

Suitable materials for constructing fasteners 44, such as sheet materials for constructing substrate member 48 and adhesive materials for constructing layer 54, are available from various manufacturers, such as 3M Company, a business having a Disposable Products Division with offices in the 3M Center, St. Paul, Minn.; and Avery International, a business having a Specialty Tape Division with offices in Painesville, Ohio.

The illustrated embodiment of the tape fastening system includes a release tape member 55 for releasably holding user-bond region 52 of the tape fastener in a storage position which protects the user-bond region of primary adhesive layer 54 against contamination or premature adhesion against other portions of diaper 20. In the illustrated embodiment, release tape 55 is positioned in a superposed, adjacent relation with substrate member 48, and is attached to an interior surface of diaper 20. The representatively shown embodiment of release tape 55 includes an anchor surface 56 and an opposite release surface 60. Anchor surface 56 has disposed thereon a suitable anchor adhesive layer 58, and release surface 60 has disposed thereon a selected layer of release coating 62, such as a coating composed of cured (cross-linked) poly dimethyl siloxane (PDMS). Suitable release tapes are commercially available from vendors such as 3M Company and Avery International.

In a particular embodiment of the invention, a terminal end portion of release tape 55 overlaps and adhesively bonds to an intermediate section of substrate member 48 along a bond region 63 which extends across the width of the substrate member. The resultant interconnection between substrate member 48 and release tape 55 provides for a Y-bond which can strengthen the assembly and attachment of tape fastener 44 to the section of diaper 20 that is clamped between release tape 55 and factory-bond region 50 of tape substrate member 48.

The user-bond region of tape substrate member 48 has a distal end section 68 which is appointed for grasping by the user to suitably position and adhere the user-bond region of tape fastener 44 to an appointed tape securement zone of the article. In the illustrated embodiment, for example, the user will typically grasp end section 68 to adhere the tape fastener against landing zone patch 42. Conventional adhesive tape fasteners have typically constructed distal end section 68 to be non-adhering and non-securing so that the end section can be more easily found and lifted by the user.

In a particular aspect of the invention, tape fastener 44 can include a separate finger tab member 70 connected to substrate end section 90 along an attachment region 72. The representatively shown overlapping-type bond may comprise an adhesive bond, sonic bond, thermal bond or the like. The finger tab may be overlapped directly against adhesive layer 54, or may be overlapped against the surface of substrate member 48 which is opposite adhesive layer 54, as desired. Where finger tab 70 connects against adhesive layer 54, substrate 48 may be configured to overlap the complete surface area of the finger tab (FIG. 8B).

In an optional configuration of the invention, finger tab 70 may be constructed by providing a particular physical or chemical treatment applied to end section 90 of substrate member 48. The treatment can be configured to impart desired absorbency and/or tactile characteristics to the gripping region of the resultant finger tab.

In the illustrated embodiment, finger tab 70 is composed of a flexible, absorbent material, such as a woven or nonwoven fabric. The fabric can have a basis weight within the range of about 7–170 gm/m$^2$ (gsm). The basis weight is preferably within the range of about 10–135 gsm and more preferably is within the range of about 34–100 gsm. In addition, the fabric can have a density within the range of about 0.02–0.6 gm/cm$^3$ (measured at 0.176 psi), and can have a thickness within the range of about 0.01–0.15 cm (measured at 0.176 psi). In particular aspects of the invention, the fabric density can be within the range of about 0.05–0.30 gm/cm$^3$, and optionally can be within the range of about 0.05–0.15 gm/cm$^3$. In further aspects of the invention, the fabric thickness can be within the range of about 0.01–0.10 cm, and may be within the range of about 0.02–0.08 cm to provided desired performance.

In yet other aspects of the invention, finger tab 70 can be composed of a material which is capable of absorbing selected amounts of contaminants, such as powders, liquids, and creams, which may be carried on the fingers of the user. In one aspect of the invention, the finger tab material, particularly the portion comprising the grasping section of the finger tab, provides for an absorbent capacity (absorbency) value of at least about 8 wt %, with respect to white mineral oil having a Saybolt viscosity of about 80–90 at 100° F. Preferably, the oil absorbency value of the finger tab is at least about 15 wt %, and more preferably is at least about 20 wt %.

Finger tab 70 may also be composed of a material which provides a tactile complement or contrast when compared to substrate member 48. In a particular aspect of the invention, for example, finger tab 70 can include a material which provides a gripping surface having a coefficient of friction value which is not less than about 0.12. Preferably, the coefficient of friction value is not less than about 0.15, and more preferably the coefficient of friction value is not less than about 0.20 to provide desired performance. For the purposes of the present invention, a suitable technique for determining the coefficient of friction value is provided by a KAWABATA, Model KES-FB-4, Surface Characteristics Testing Apparatus, a device produced by KATO TECH Co. Ltd, Kyoto, Japan and available from TEX-MAC, a business having offices located at Charlotte, N.C. The apparatus includes a test method for measuring a coefficient of friction value designated "MIU".

In another aspect of the invention, for example, finger tab 70 can include a material which is configured to provide gripping surface having a surface roughness value which is not less than about 2.75 micrometers. Preferably, the surface roughness value is not less than about 3.00 micrometers, and more preferably, the surface roughness value is not less than about 3.2 micrometers to provide desired performance. A suitable technique for determining the surface roughness value is the aforementioned KAWABATA Surface Characteristics Testing Apparatus. The apparatus includes a test method for measuring a surface roughness value designated "SMD".

Finger tab 70 may also be composed of a material which facilitates the location and lifting of the tab by the user. In a particular aspect of the invention, finger tab 70 can have an average stiffness value of not more than about 148 grams. Preferably, the finger tab has an average stiffness value of not more than about 100 grams, and more preferably, has an average stiffness value of not more than about 75 grams to provide desired performance. More particular embodiments of the invention may include configurations of the finger tab having a more grippable or more absorbent surface arranged to face inwardly, toward the body of the wearer of the article. Accordingly, the non-adhering side of the tape substrate material would face outwardly of the article. Thusly configured, the finger tab has designated, one-directional stiffness value exhibited when the finger tab is being bent away from the wearer's body. In this regard, a more particular aspect of the invention finger tab 70 can have an average designated stiffness value of not more than about 40 grams. Preferably, the finger tab has an average designated stiffness value of not more than about 37 grams, and more preferably, has an average designated stiffness value of not more than about 35 grams to provide desired performance.

A suitable technique for determining the average stiffness values, particularly the designated average stiffness values, employs a Handle-O-Meter, such as Model No. 211-5 with flat plates and digital readout. The device is available from Thwing-Albert Instrument Company, a business having offices in Philadelphia, Pa. The testing procedure conforms to INDA Standard Test IST 90.0–75 (R82) at a gap width of 20 mm, except for the following modifications: (a) the specimen size measures 4 in×4 in; and (b) five specimens, instead of two, are tested from each sample.

With still a further aspect of the invention, finger tab 70 can be configured to provide a visually contrasting appearance when compared to substrate member 48. For example, the finger tab may be colored or may include printed graphics which can help to visually distinguish the finger tab from other portions of diaper 20. In preferred configurations, the peripheral end contour of the finger tab is curved and substantially free of sharp corners which might excessively irritate the skin of the wearer.

Finger tab 70 includes a inward bodyside surface 86 and an outward surface 88. In addition, the finger tab has a length dimension 80 and a width dimension 82. In particular aspects of the invention, the finger tab length is within the range of about 6–22 mm, preferably is within the range of about 8–19 mm, and more preferably is within the range of about 9–16 mm. The finger tab width is within the range of about 19–38 mm, more preferably is within the range of about 22–35 mm, and more preferably is within the range of about 25–32 mm.

Accordingly, the grasping area provided by the finger tab is at least about 39 mm$^2$, more preferably is at least about 128 mm$^2$, and more preferably is at least about 253 mm$^2$. In preferred arrangements, the grasping area provided by finger tab 70 is within the range of about 75–150 mm$^2$.

In other aspects of the invention, the finger tab has a length divided by width quotient which is within the range of about 0.16–1.16. Preferably, the length-to-width quotient is within the range of about 0.23–0.86, and more preferably is within the range of about 0.28–0.64 to provide desired performance attributes.

The grasping area of the finger tab in combination with the selected dimensions of the finger tab can help increase the area of the finger tab which makes actual contact with the user's thumb and finger during grasping. As a result, the user can more readily hold the tab and can better avoid contact with the primary adhesive layer 54.

The ease of gripping the finger tab may be increased when the general shape of the finger tab approximately matches the shape of the gripping thumb and finger. With a nested finger tab configuration, such as shown in FIG. 8B, the grasping area provided by the finger tab is at least about 20 mm$^2$, more preferably is at least about 64 mm$^2$, and more preferably is at least about 127 mm$^2$. In preferred arrangements, the grasping area provided by finger tab 70 is within the range of about 37–75 mm$^2$.

With reference to FIGS. 3–3A, another aspect of the invention provides a tape fastener 44 having a substrate member 48 which defines a factory-bond section 50 and a user-bond section 52. The user-bond section includes a primary layer of adhesive 54, and is connected to a finger tab 70 which has a substantially non-securing grasping section 71 thereof. The finger tab connects to substrate member 48 along a fixed end region 72 of the finger tab. Fixed region 72 extends along the width dimension, and preferably along the entire width, of tape substrate 48 and includes a supplemental adhesive layer 94 thereon. The supplemental adhesive has a relatively higher peel strength value than primary adhesive 54, as determined with respect to adhesion to the appointed tape securement zone of the article, such as landing zone patch 42. In particular embodiments of the invention, supplemental adhesive 94 can be configured to provide a relatively higher shear strength value than primary adhesive 54, as determined with respect to adhesion to the appointed tape securement zone. In the illustrated embodiment, supplemental adhesive 94 is disposed on a securement section 84 of finger tab 70. In particular embodiments of the invention, supplemental adhesive 94 provides for an adhesive peel value (at 180° peel) of at least about 200 gm. Preferably, the adhesive peel value is at least about 300 gm, and more preferably, the adhesive peel value is at least about 400 gm. A suitable procedure for determining the adhesive peel value is method PSTC-4 (Pressure Sensitive Tape Council).

The relatively higher adhesive strength parameters of supplemental adhesive 94 can advantageously provide greater resistance to undesired pop-opens. In addition, the greater adhesive strength of the supplemental adhesive can help make tape fastener 44 less susceptible to manipulation by the wearer. As a result, the wearer is less likely to initiate premature openings of the tape fastener.

Particular embodiments of tape fastener 44 can be configured such that supplemental adhesive 94 provides for a peel strength which is at least about 1.5 times the peel strength of primary adhesive 54. Preferably, the supplemental adhesive provides for a peel strength which is at least about 1.75 times the peel strength of adhesive 54, and more preferably, is configured to provide a peel strength which is at least about 2 times the peel strength of the primary adhesive.

In addition, supplemental adhesive 94 can be configured to provide an adhesive shear strength which is at least 1.5 times the shear strength of primary adhesive 54. Preferably, the shear strength of the secondary adhesive is at least about 1.75 times the shear strength of primary adhesive 54, and more preferably is at least about 2 times the shear strength of the primary adhesive.] In particular embodiments of the invention, supplemental securement section 84 has an area which extends over at least about 60 mm$^2$, and preferably has an area which extends over at least about 100 mm$^2$. In the illustrated embodiment, supplemental adhesive 94 extends across the total width dimension 66 of substrate member 48. Optionally, the supplemental adhesive may extend across only a portion of the width of the substrate member. In alternative embodiments, the supplemental adhesive may be selectively positioned and restricted to limited shoulder edges 78 (FIG. 4) of tape fastener 44. Further alternative embodiments may have the supplemental adhesive 94 configured as a layer laminated to and covering over a portion of primary adhesive 54.

The material of finger tab 70 may be substantially coextensive with the width of substrate end section 90, and may substantially end at the longitudinally terminal edge. Alternatively, finger tab 70 may extend beyond the terminal edge of the tape substrate member.

With reference to FIGS. 4–4A, another aspect of the invention provides a tape fastener 44 which comprises a tape substrate member 48 having a user-bond section 52 which includes a terminal end region 46. The terminal end region has a generally concave peripheral outline 76, and the resultant peripheral contour of terminal end region 46 defines a selected indented area 92. A primary adhesive layer 54 extends over an appointed facing surface of substrate member 48. As a result, substrate member 48 includes adhesive bearing shoulder edges 78 which bracket concave section 76 and bracket indented area 92.

A particular embodiment of the invention can be configured with a layer of absorbent material which overlies and covers indented area 92. The absorbent material may, for example, comprise a nonwoven fabric, such as a spunbond fabric, meltblown fabric or a foam material. In the illustrated embodiment, a finger tab layer 70 is attached to the surface of substrate member 48 which is opposite primary adhesive layer 54. The attachment between finger tab 70 and substrate member 48 may employ any suitable mechanism, such as adhesive bonding, sonic bonding, thermal bonding, pinning, crimping, or the like.

In the configuration of the invention representatively shown in FIG. 4, the finger tab material overlying indented area 92 provides a convenient, unaffixed terminal edge 74 which is loose and can be readily located and grasped by the user. At the same time, the sections of shoulder adhesive 85 positioned on the bracket or shoulder sections 78 at the end of tape fastener 44 hold the peripheral edges and corners of the user-bond region 52 attached to the securement zone of the article. As a result, the shoulder sections of the tape fastener can be less susceptible to peeling forces which might prematurely open the fastener. The adhered shoulder sections can also be less susceptible to manipulation and opening by a child.

With reference to FIGS. 5–5B, yet another aspect of the invention can include a tape fastener 44 having a factory-bond section 50 and a user-bond section 52. The user-bond section includes a primary layer of adhesive 54 thereon and has a terminal region 46 connected along a fixed end region 72 of a finger tab 70. The finger tab has a substantially non-securing grasping section 71 thereof and has a distal width dimension 108 which is less than the width dimension of the terminal end section 46 of substrate member 48. Optionally, a section of supplemental adhesive 94 can be positioned at the terminal end section of substrate 48. In the shown embodiment, the supplemental adhesive is located adjacent finger tab bond 72.

As representatively shown in FIG. 5B, at least a portion of finger tab 70 can be selectively positionable to a location which is interposed between primary adhesive layer 54 and the factory-bond, securement region of backsheet 22 against which tape fastener 44 is adhered to hold diaper 20 on the wearer. In the illustrated embodiment, the selected positioning can be accomplished by folding finger tab back against adhesive 54 on tape substrate 48 (FIG. 5B). When interposed between substrate member 48 and backsheet 22, the side edges of the interposed portion of finger tab 70 lie adjacent a pair of adhesive-bearing, shoulder sections 78. Accordingly, the interposed portion of finger tab 70 is bracketed by adhesive-bearing, shoulder sections of substrate member 48.

It should be noted that finger tab 70 may be attached to the surface of substrate 48 which has the layer of primary adhesive thereon. Alternatively, finger tab 70 may be attached to the surface of substrate member 48 which is located opposite adhesive layer 54.

The embodiment of the invention representatively shown in FIG. 5 can be selectively employed in two different modes. In the first mode, finger tab 70 is left exposed in a freely extended position to provide a relatively larger grasping section which can be easily located and manipulated by the user. In the second mode, finger tab 70 is tucked away in a restrained, retracted position. During use, the finger tab becomes juxtaposed between substrate member 48 and the appointed landing zone region of backsheet 22 to minimize the exposure of the finger tab to the exploring hands of an inquisitive child. As a result, the user can choose to either have a grasping section that is readily accessible to the user or have a grasping section that is less accessible to the child.

Figure 6A:
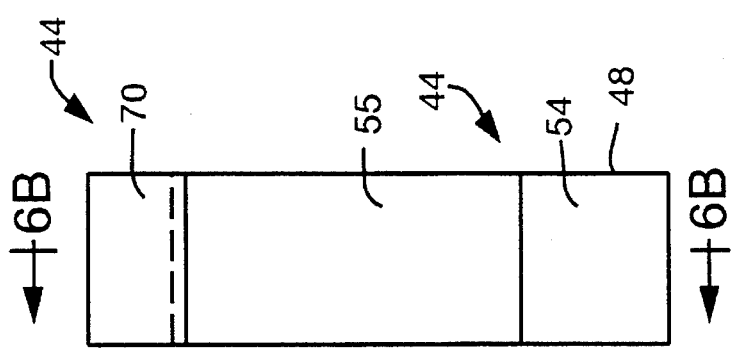
FIGS. 6–6B representatively show a method for producing an interconnected plurality of adhesive fastening tapes constructed in accordance with the present invention.
Figure 6:
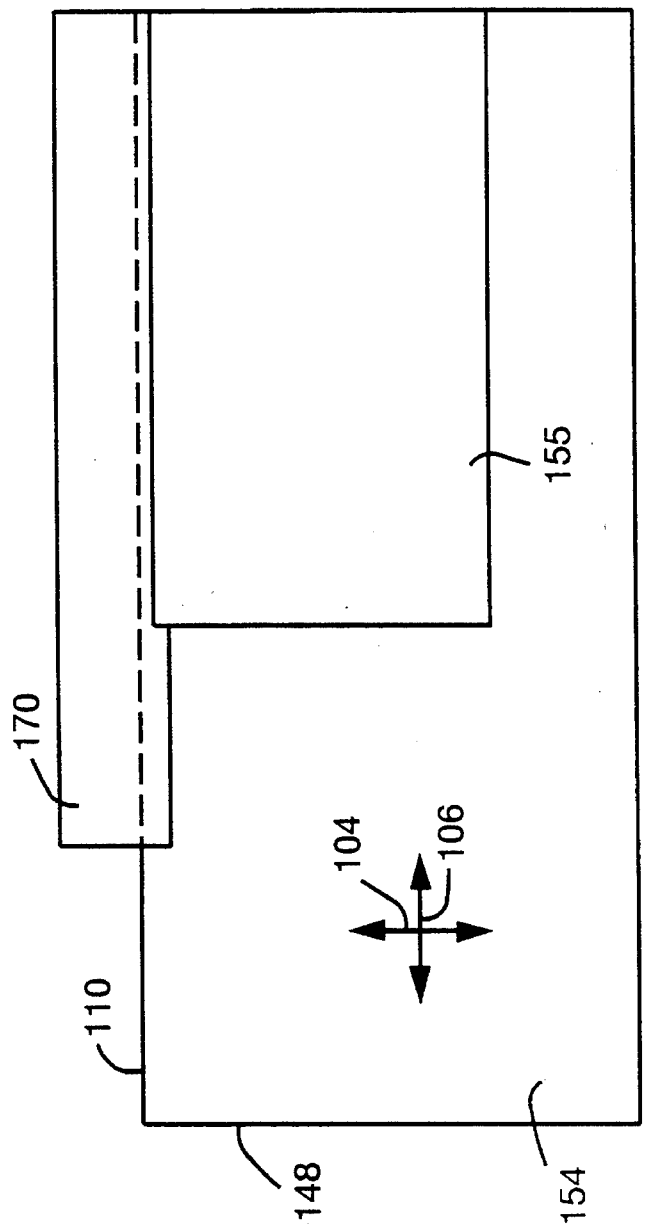
Figure 6B:
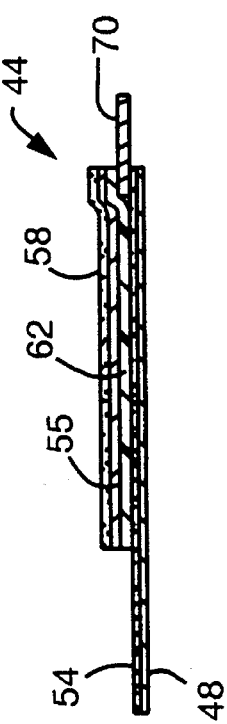

With reference to FIGS. 6–6B, a process aspect of the invention provides a distinctive method for forming a plurality of tape fasteners 44 comprising a finger tab element 70 assembled onto a substrate member 48. The process can be employed in-line with an operation for manufacturing a selected article, such as a disposable diaper, incontinence garment, feminine care article, gown, garment or the like. The resultant process can be configured to rapidly form a plurality of individual tape fasteners and then assemble the fasteners to the selected article. The process can also be configured to assemble a release tape component to the article, as desired.

In the process embodiment illustrated in FIGS. 6–6B, a web of substrate material 148 has a cross-directional width dimension 104 and a longitudinal length dimension 106. The length dimension extends along the path of movement of web 148 through the manufacturing machinery. Accordingly, length dimension 106 is typically referred to as the machine direction of the web. Substrate web 148 has applied thereon a layer of primary adhesive 154. A web of finger tab material 170 is positioned in overlapping relation with a lateral side edge 110 of substrate web 148. The portion of primary adhesive 154 positioned between substrate web 148 and finger tab web 170 bonds the substrate web to the finger tab web to form an assembly. A web of release tape material 155 can then be applied onto the exposed surface of primary adhesive 154, with the release coating surface 62 of the release tape positioned against the layer of primary adhesive and with the anchor adhesive 58 of the release tape exposed for subsequent assembly onto an individual selected article. A suitable cutting mechanism (not shown) can then be employed to separate the assembled composite web into individual tape fasteners 44. In the particular embodiment representatively shown in FIG. 6, a relatively smaller narrow band of finger tab web 170 is adhered to substrate web 148 with a majority of the finger tab web extending away from substrate side edge 110. In alternative process embodiment, finger tab material 170 can be configured such that a relatively smaller portion of finger tab material 70 extends past the lateral side edge 110 of substrate web 148 with the majority of finger tab material 170 adhered to substrate web 148. In yet another process embodiment, finger tab material 170 can be configured such that substantially no portion of finger tab material 70 extends past the lateral side edge of the substrate web.

In a further process embodiment representatively shown in FIGS. 7–7B, substrate web material 148 can comprise a generally continuous web having a cross-directional width which is a selected multiple of the desired length of the substrate material 48 employed for each tape fastener 44. For example, substrate web material 148 can have a cross-directional width which is approximately two times the desired length of substrate material 48 in an individual tape fastener 44. Substrate web material 148 is provided with a substantially continuous adhesive layer 154 disposed upon a facing surface thereof.

A strip of finger tab material 170 is adhered or otherwise attached to substrate web material 148 along a selected medial section of the substrate material to form a composite. In the illustrated embodiment, finger tab material 170 is substantially centered along the longitudinal centerline of substrate material 148 and is placed against adhesive 154. The cross-directional width of finger tab material 170 is a selected multiple of the desired length of each finger tab 70 on an individual tape fastener 44. The illustrated embodiment, for example, employs a web of finger tab material 170 which has a cross-directional width of approximately two times the length of an individual finger tab on a tape fastener. Web layers of release tape material 155 are placed against adhesive layer 154 on each side of appointed separation line 112. The release coating surface 62 of the release tape is positioned against the layer of primary adhesive, and the anchor adhesive 58 of the release tape is exposed for subsequent assembly onto a selected article. A suitable separating mechanism (not shown), such as a rotary die cutter or a ultrasonic rotary cutter, can cut through the assembled substrate and finger tab materials along separation line 112 to provide substantially matched, mirror image fastener subassemblies 114 and 115. The fastener subassemblies can then, in turn, be separated into individual tape fasteners 44.

Figure 8:
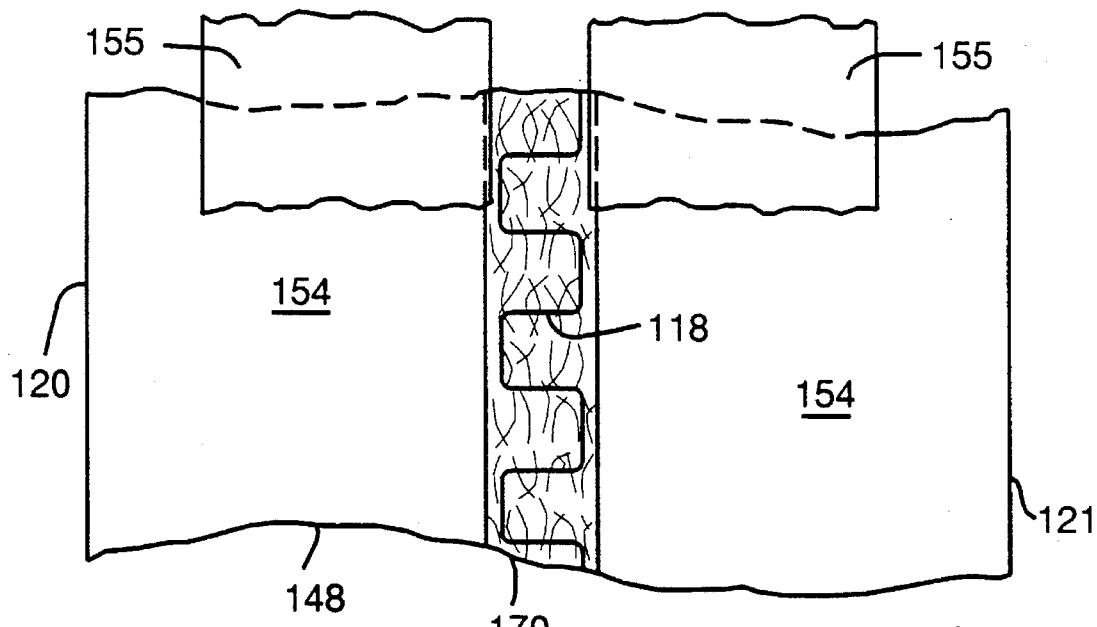
FIGS. 8–8B representatively show a method of producing an interconnected plurality of nested adhesive tapes constructed in accordance with the invention.
Figure 8A:
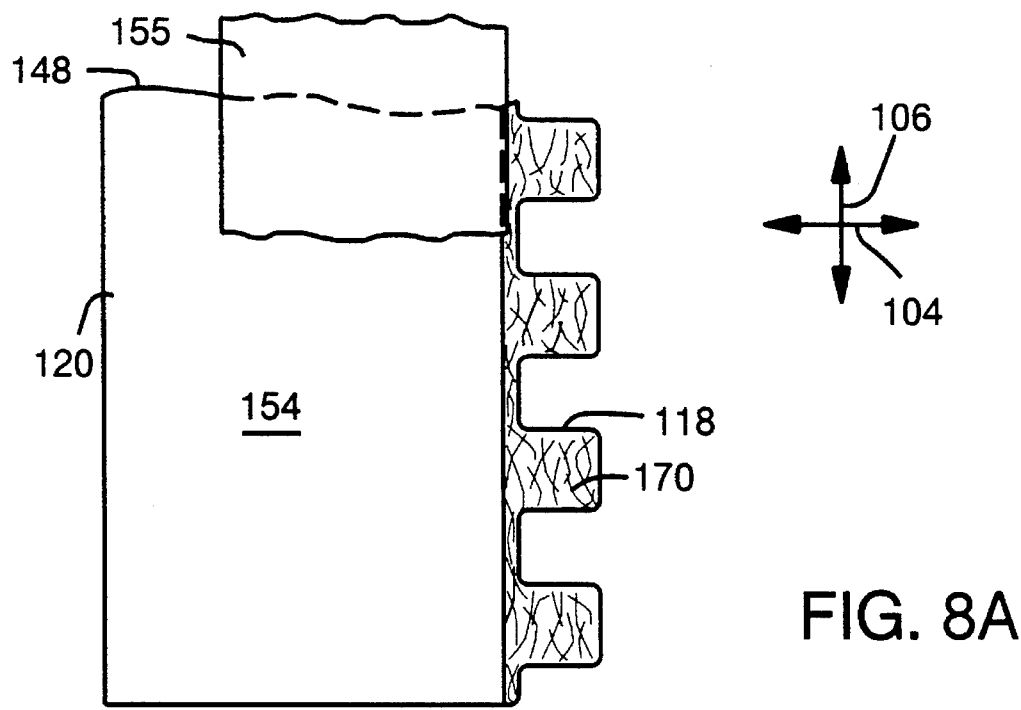
Figure 8B:
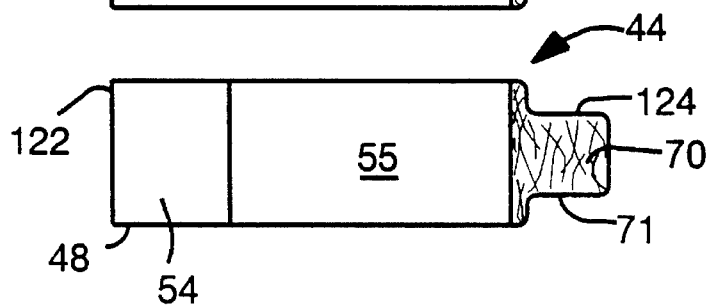

Another aspect of the process of the invention is representatively shown in FIGS. 8, 8A and 8B. In the illustrated embodiment, substrate material 148 is a substantially continuous web which has a layer of adhesive 154 disposed on a major facing surface thereof. Substrate web 148 has a cross-directional width which is slightly less than two times the desired length of an individual substrate member 48.

A ribbon of finger tab material 170 comprises a substantially continuous web which is adhered or otherwise connected to substrate web 148 to form a composite. Finger tab web 170 is located along a selected medial section of substrate web 148. In the shown embodiment, finger tab material 170 is substantially centered along the longitudinal centerline of substrate material 148 and adhered to primary adhesive layer 154. In the illustrated embodiment, the ribbon of finger tab material 170 has a width, measured along cross-direction 104, which is equal to or slightly greater than the desired cross-directional extent of an individual finger tab 70. Web layers of release tape material 155 are placed against adhesive layer 154 on each side of appointed separation line 112. The release coating surface 62 of the release tape is positioned against the layer of primary adhesive, and the anchor adhesive 58 of the release tape is exposed for subsequent assembly onto a selected article.

A suitable cutting mechanism (not shown), such as a rotary die cutter or an ultrasonic rotary cutter, can be constructed and arranged to produce a serpentine cut 118 through the assembly composed of finger tab material 170 and substrate material 148. The curvilinear serpentine cut extends generally along the length of the composite and periodically undulates along the cross-direction of substrate material 148. The serpentine cut produces a pair of nested fastener subassemblies 120 and 121. Each nested subassembly comprises an interconnected plurality of individual, nested-type fasteners 122. A conventional cutting mechanism (not shown) can be employed to generate suitable cross-directional cuts to operably separate the nested subassemblies 120 and 121 into the individual nested fasteners. As a result, each fastener 122 can have a finger tab 70 with a curvilinear end periphery 124, and the substrate material 148 is substantially coextensive with the entirety of finger tab 70.

In the illustrated embodiment, nested fasteners 122 formed from subassembly 120 are substantially of equal size and are approximately mirror images of the complementary fasteners formed from subassembly 121. The tape fasteners produced from nested subassembly 120 are slightly offset from the fasteners produced from nested subassembly 121 by a discrete distance along the length dimension of substrate material 148. More particularly, nested fastener 122 is offset from its opposed counterpart fastener by approximately one-half of the desired width dimension of an individual tape fastener 44. In the illustrated embodiment of serpentine cut 118, the serpentine cut stops short of the lateral of finger tab web 170 along cross-direction 104.

Figure 9:
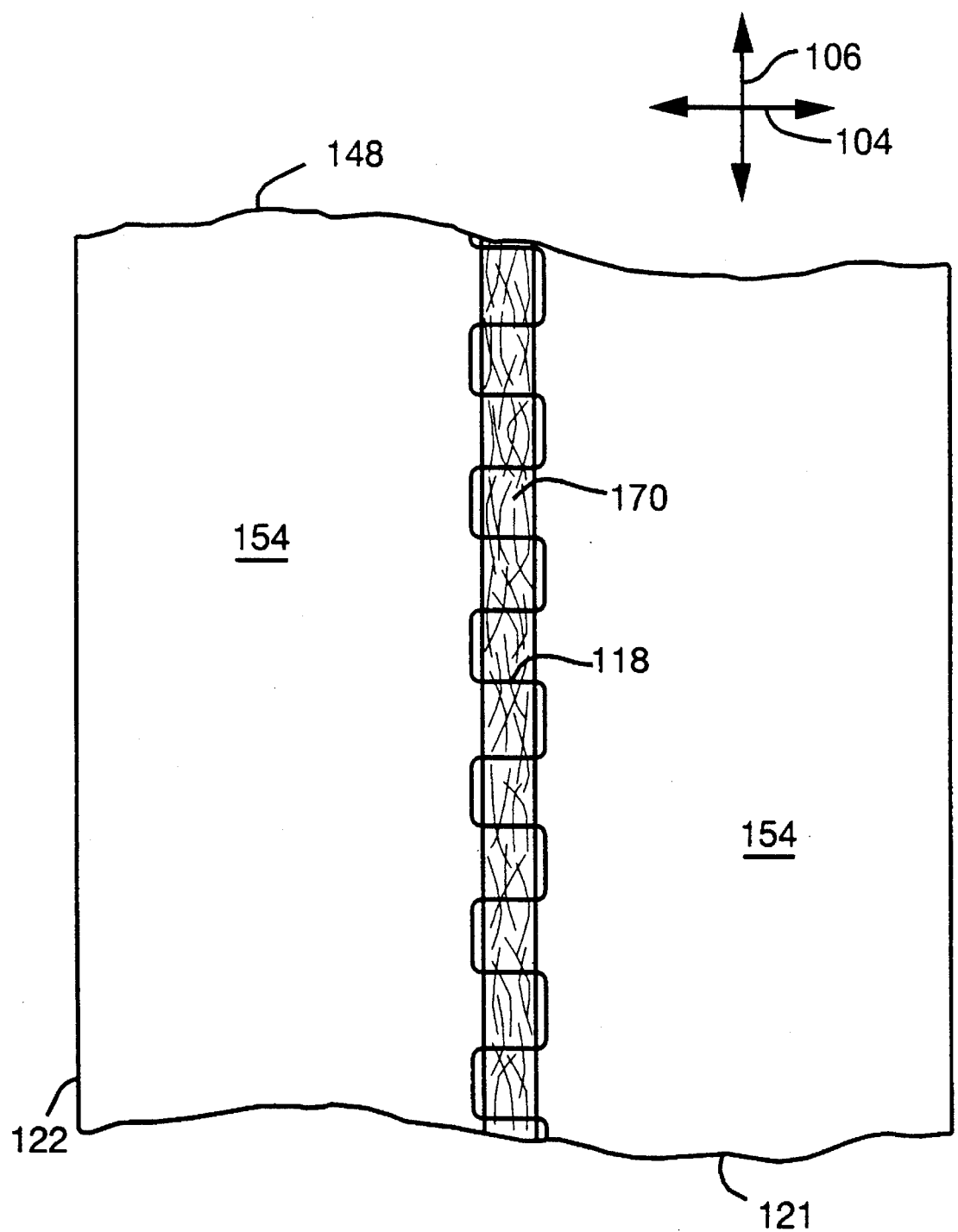
FIG. 9 representatively shows another method of producing an interconnected plurality of nested adhesive tapes constructed in accordance with the invention.

Optionally, the cross-directional extent of serpentine cut 118 may substantially coincide with the cross-directional, terminal edge boundaries of the finger tab web, or may extend beyond the lateral edge boundaries of the finger tab material, as representatively shown in FIG. 9.

The following Examples are provided to give a more detailed understanding of the invention. The particular amounts, proportions, compositions and parameters are meant to be exemplary, and are not intended to specifically limit the scope of the invention.

EXAMPLES

Examples 1–12

The following samples of finger tab materials were constructed, and had the following configurations:

Sample 1: This sample was a composite of a 0.4 osy (ounce per square yard) fabric adhesively laminated to a tape tab composed of 0.1 mm thick polypropylene sheet. The polypropylene film sheet for constructing the various Samples was a tape material obtained from Avery International. The fabric was a spunbond, nonwoven fabric having an Expanded Hanson Pennings (EHP) bond pattern. The fabric density was about 0.060 g/cc (at 0.176 psi), and the fiber denier was about 2.0.

Sample 2: This sample was a composite of a 1.0 osy (ounce per square yard) fabric adhesively laminated to a tape tab composed of 0.10 mm thick polypropylene sheet. The fabric was a spunbond, nonwoven fabric having a EHP bonding pattern. The fabric density was about 0.080 g/cc (at 0.176 psi), and the fiber denier was about 2.0.

Sample 3: This sample was a composite of a 2.0 osy (ounce per square yard) fabric adhesively laminated to a tape tab composed of 0.10 mm thick polypropylene sheet. The fabric was a spunbond, nonwoven fabric having a EHP bonding pattern. The fabric density was about 0.110 g/cc (at 0.176 psi), and the fiber denier was about 2.0.

Sample 4: This sample was a composite of a 3.0 osy (ounce per square yard) fabric adhesively laminated to a tape tab composed of 0.10 mm thick polypropylene sheet. The fabric was a spunbond, nonwoven fabric having a EHP bonding pattern. The fabric density was about 0.146 g/cc (at 0.176 psi), and the fiber denier was about 2.0.

Sample 5: This sample was a layer of 2.0 osy (ounce per square yard) spunbond, nonwoven fabric having a EHP bonding pattern. The fabric density was about 0.110 g/cc (at 0.176 psi), and the fiber denier was about 2.0.

Sample 6: This sample was a composite of a 0.5 osy (ounce per square yard) fabric adhesively laminated to a tape tab composed of 0.10 mm thick polypropylene sheet. The fabric was a spunbond, non-woven fabric having a wire-weave bonding pattern. The fabric density was about 0.078 g/cc (at 0.176 psi), and the fiber denier was about 2.65.

Sample 7: This sample was a composite of a 1.0 osy (ounce per square yard) fabric adhesively laminated to a tape tab composed of 0.10 mm thick polypropylene sheet. The fabric was a spunbond, nonwoven fabric having a wire-weave bonding pattern, and had a density of about 0.102 g/cc (at 0.176 psi). The fabric was composed of fibers having a fiber denier of about 2.65.

Sample 8: This sample was a composite of a 2.0 osy (ounce per square yard) fabric adhesively laminated to a tape tab composed of 0.10 mm thick polypropylene sheet. The fabric was a spunbond, nonwoven fabric having a wire-weave bonding pattern, and had a density of about 0.145 g/cc (at 0.176 psi). The fabric was composed of fibers having a fiber denier of about 2.65.

Sample 9: This sample was a composite of a 2.5 osy (ounce per square yard) fabric adhesively laminated to a tape tab composed of 0.10 mm thick polypropylene sheet. The fabric was a spunbond, nonwoven fabric having a wire-weave bonding pattern, and had a density of about 0.168 g/cc (at 0.176 psi). The fabric was composed of fibers having a fiber denier of about 2.65.

Sample 10: This sample was a composite of a 1.8 osy (ounce per square yard) fabric adhesively laminated to a tape tab composed of 0.10 mm thick polypropylene sheet. The fabric was a laminated composite fabric composed of a first spunbond nonwoven fabric layer, a meltblown nonwoven fabric layer, and a second spunbond nonwoven fabric layer. The first spunbond layer was composed of polypropylene fibers and had a basis weight of about 0.4 osy. The meltblown layer was composed of polypropylene fibers and had a basis weight of about 1.0 osy. The second spunbond layer was composed of polypropylene fibers and had a basis weight of about 0.4 osy. The density of the composite fabric was about 0.109 g/cc, and the fibers in the spunbond layers had a denier of about 2.

Sample 11: A composite composed of a 0.01 mm thick layer of polypropylene sheet adhesively laminated to a tape tab composed of 0.01 mm thick polypropylene sheet.

Sample 12: A composite composed of a 0.01 mm thick layer of polypropylene adhesively laminated to a tape tab composed of 0.01 mm thick polypropylene sheet.

Absorbent capacity values and Gurley stiffness values were determined for each of Samples 1–12. These data are summarized in the following TABLE 1.

TABLE 1

| Sample No. | Absorbent Capacity (wt % oil) | Gurley Stiffness (mm) |
| --- | --- | --- |
| 1 | 4.46 | 204.9 |
| 2 | 1.08 | 85.4 |
| 3 | 8.86 | 156.5 |
| 4 | 46.72 | 489.5 |
| 5 | 39.80 | 10.3 |
| 6 | 1.93 | 131.9 |
| 7 | 1.78 | 231.6 |
| 8 | 15.41 | 531.1 |
| 9 | 28.97 | 674.9 |
| 10 | 60.47 | 316.3 |
| 11 | 0.52 | 953.5 |
| 12 | 0.04 | 928.0 |

Testing: For the purposes of the present invention, a suitable technique for determining the oil absorbent capacity value of a finger tab region employs the following test:

Oil Absorption Against a Negative Head (10 cm)

Figure 10:
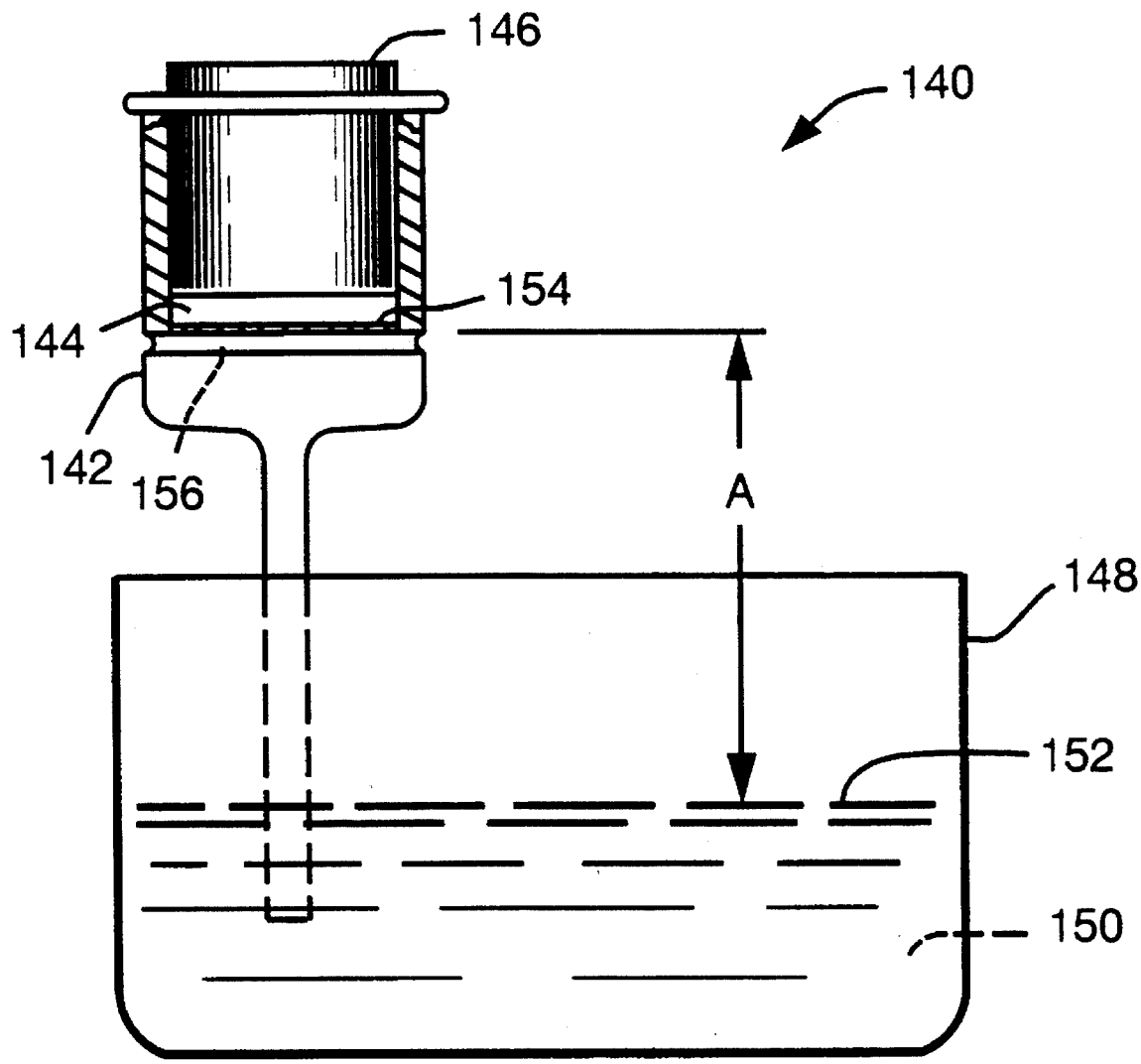
FIG. 10 representatively shows a testing apparatus for measuring the oil absorbent capacity of a sample of test material.

The oil absorption test apparatus 140 is representatively shown in FIG. 10.

Equipment 1. 150 ml Buchner Form Fritted Glass (142), Coarse, Pyrex® brand glass, Corning No. 36060. Available from Scientific Products #F7356-24.

2. 5.1 cm (2") circular die.

3. 5.4 cm (2⅛") circular Lucite® disc (144), 6.4 mm (¼") thick.

4. Brass weight (146) to give 0.028 kgs/cm² (0.4#/in²). Brass weight and Lucite disc to weigh 569±grams.

5. Reservoir (148) for oil (150)—a container capable of holding approximately 2 liters or more of liquid.

6. Balance—capable of weighing to the nearest 0.0001 gram.

7. Timer.

Solution

Blandol white mineral oil @80/90 Saybolt Viscosity at 100° F., available from WITCO Chemical, a business having offices at 520 Madison Avenue, New York, N.Y.

Procedure

1. When not in use, keep the test apparatus loaded with a non-test sample to prevent air entrapment in the fritted filter (156). Prior to testing, remove the non-test sample and wipe the Lucite® disc (144) clean.

2. Bring oil (150) up to line (152) on reservoir (148) to give a 10 cm negative head on the oil. Maintain the temperature of the oil at 21°±4° C. (70°±7° F.).

3. Using the 2" circular die, stamp out a sample (154) of test material and weigh to the nearest 0.0001 gram.

4. Weigh and record the weight, to the nearest 0.0001 gram, of the Lucite disc (144).

5. Place the sample (154) on the filter (156). Then place the Lucite disc on top of the sample.

6. Add the weight (146) onto the top of the Lucite disc. Remove the weight after two minutes have elapsed.

7. Remove the Lucite disc and the sample and weigh them together to the nearest 0.0001 gram.

8. Subtract the original sample and disc weight from the final sample and disc weight to determine the amount (grams) of oil absorbed.

9. Divide the amount (grams) of oil absorbed by the sample weight and multiply the result by 100 to obtain percent absorbed.

$$\% \text{ absorbed} = \frac{\text{grams of oil absorbed (item 8)}}{\text{gram weight of sample (item 3)}} * 100$$

10. Report as percent absorbed (percent by weight).

Having thus described the present invention in rather full detail, it will be readily apparent to a person of ordinary skill that various changes and modifications can be made without departing from the spirit of the invention. All of such changes and modifications are contemplated as being within the scope of the present invention, as defined by the subjoined claims.

We claim:

1. An article having first and second waistband sections and an intermediate section which interconnects said waistband sections, said article comprising:

a backsheet layer;

a liquid permeable topsheet layer superposed in facing relation with said backsheet layer;

an absorbent body interposed between said backsheet and topsheet layers; and at least one adhesive tape member connected to said first waistband section, said tape member having a factory-bond section for connecting said tape member to said first waistband section and a user-bond section for connecting to said second waistband section to secure said article on a wearer, said user-bond section including a primary layer of adhesive thereon for adhering to an appointed tape securement zone of said backsheet layer, said user-bond section connecting to a finger tab which has a substantially non-attaching grasping section thereof, said finger tab fixedly attached to said tape member along a fixed end region of said finger tab, said fixed end region of said finger tab including a supplemental layer of adhesive directly thereon for adhering to said appointed tape securement zone of said backsheet layer, and said supplemental adhesive having a higher peel strength value than said primary adhesive, as determined with respect to adhesion to said appointed tape securement zone of said backsheet layer.

2. An article as recited in claim 1 wherein said supplemental adhesive has a higher shear strength value than said primary adhesive, as determined with respect to adhesion to said appointed tape securement zone.

3. An article as recited in claim 1 wherein said finger tab grasping section comprises an exposed layer of absorbent material.

4. An article having first and second waistband sections and an intermediate section which interconnects said waistband sections, said article comprising:

a backsheet layer a liquid permeable topsheet layer superposed in facing relation with said backsheet layer;

an absorbent body interposed between said backsheet and topsheet layers; and at least one adhesive tape member connected to said first waistband section, said tape member having a factory-bond section for connecting said tape member to said first waistband section and a user-bond section for connecting to said second waistband section to secure said article on a wearer, said user-bond section including a primary layer of adhesive thereon and having a terminal region connected along a fixed end region of a finger tab which has a substantially non-attaching grasping section thereof, said finger tab having a maximum width dimension which is less than a width dimension of said terminal section of said tape member, said finger tab being selectively positionable to a location which is interposed between said tape member and said backsheet when said tape member is employed to secure said article on the wearer, said interposed location bracketed by said primary adhesive.

5. An article as recited in claim 4 wherein said finger tab grasping section comprises a layer of absorbent material.

6. An article having first and second waistband sections and an intermediate section which interconnects said waistband sections, said article comprising:

a backsheet layer;

a liquid permeable topsheet layer superposed in facing relation with said backsheet layer;

an absorbent body interposed between said backsheet and topsheet layers;

at least one adhesive tape member connected to said first waistband section, said tape member having a factory-bond section for connecting said tape member to said first waistband section and a user-bond section for connecting to said second waistband section to secure said article on a wearer, said user-bond section including a primary adhesive layer located on a first surface of said tape member and including a terminal end region thereof which has a generally concave peripheral outline, said concave outline defining an indented area which is substantially free of exposed adhesive and extends inwardly from a longitudinally terminal, end edge of said tape member; and a finger tab connected to said user-bond section and attached to a second surface of said tape member, said second surface located opposite of said primary adhesive layer, and said finger tab including a non-securing grasping section thereof which overlies said indented area.

7. An article as recited in claim 6, wherein said finger tab grasping section includes a layer of absorbent material having an absorbent capacity value of at least about 8 wt %.

8. An article as recited in claim 6, wherein said absorbent material has an absorbent capacity value of at least about 15 wt %.

9. An article having first and second waistband sections and an intermediate section which interconnects said waistband sections, said article comprising:

a backsheet layer;

a liquid permeable topsheet layer superposed in facing relation with said backsheet layer;

an absorbent body interposed between said backsheet and topsheet layers;

at least one adhesive tape member connected to said first waistband section, said tape member having a factory-bond section for connecting said tape member to said first waistband section and a user-bond section for connecting to said second waistband section to secure said article on a wearer, said user-bond section including a primary adhesive layer located on a first surface of said tape member and including a terminal end section having a width dimension thereof; and a finger tab connected to said user-bond section and attached to said first surface of said tape member, said finger tab having a tab width which is less than said width of said end section of said tape member, said finger tab providing a grasping section which defines a generally concave indented area which is substantially free of exposed adhesive and extends inwardly from a terminal end edge of said end section with said finger tab bracketed by said primary adhesive.

10. An article as recited in claim 9, wherein said finger tab grasping section includes a layer of absorbent material having an absorbent capacity value of at least about 8 wt %.

11. An article as recited in claim 10, wherein said material of said grasping section includes a surface having a coefficient of friction of not less than about 0.15.

12. An article as recited in claim 1, wherein said supplemental adhesive extends across only a portion of the width of said tape member.

13. An article as recited in claim 12, wherein said supplemental adhesive is limited to shoulder edges of said tape member.

14. An article as recited in claim 4, wherein said tape member has a supplemental layer of adhesive thereon, said supplemental adhesive has a higher peel strength value than said primary adhesive, as determined with respect to adhesion to an appointed tape securement zone of said article, said supplemental adhesive extends across only a portion of the width of said tape member, and said supplemental adhesive is limited to shoulder edges of said tape member.

15. An article as recited in claim 6, wherein said tape member has a supplemental layer of adhesive thereon, said supplemental adhesive has a higher peel strength value than said primary adhesive, as determined with respect to adhesion to an appointed tape securement zone of said article, said supplemental adhesive extends across only a portion of the width of said tape member, and said supplemental adhesive is limited to shoulder edges of said tape member.

16. An article as recited in claim 9, wherein said tape member has a supplemental layer of adhesive thereon, said supplemental adhesive has a higher peel strength value than said primary adhesive, as determined with respect to adhesion to an appointed tape securement zone of said article, said supplemental adhesive extends across only a portion of the width of said tape member, and said supplemental adhesive is limited to shoulder edges of said tape member.

* * * * *